(12) United States Patent
Philipp

(10) Patent No.: US 7,147,352 B2
(45) Date of Patent: Dec. 12, 2006

(54) PRECISION LIGHT EMITTING DEVICE

(75) Inventor: Christopher Donald Philipp, Portage, MI (US)

(73) Assignee: Howmedica Leibinger, Inc., Kalamazoo, MI (US)

( * ) Notice: Subject to any disclaimer, the term of this patent is extended or adjusted under 35 U.S.C. 154(b) by 182 days.

(21) Appl. No.: 10/601,716

(22) Filed: Jun. 23, 2003

(65) Prior Publication Data
US 2004/0257817 A1 Dec. 23, 2004

(51) Int. Cl.
*F21S 13/10* (2006.01)
(52) U.S. Cl. .................. 362/363; 362/800; 257/98
(58) Field of Classification Search ............. 362/186, 362/261, 264, 307, 310, 363, 800; 257/98; 359/359
See application file for complete search history.

(56) References Cited

U.S. PATENT DOCUMENTS

| | | | |
|---|---|---|---|
| 3,218,509 A * | 11/1965 | Ploetz | 362/261 |
| 3,715,636 A * | 2/1973 | Jaffe et al. | 257/98 |
| 3,892,974 A | 7/1975 | Ellefson et al. | 250/568 |
| 4,988,375 A | 1/1991 | Bornhauser | 65/59.4 |
| 5,365,345 A * | 11/1994 | Propst et al. | 359/359 |
| 5,366,178 A | 11/1994 | Hsiong et al. | 244/3.16 |
| 5,415,655 A | 5/1995 | Fuller et al. | 606/16 |
| 5,663,639 A | 9/1997 | Brown et al. | 324/96 |
| 5,707,368 A | 1/1998 | Cozean et al. | 606/15 |
| 5,814,416 A | 9/1998 | Dodabalapur et al. | 428/690 |
| 6,096,029 A | 8/2000 | O'Donnell, Jr. | 606/9 |
| 6,106,514 A | 8/2000 | O'Donnell, Jr. | 606/9 |
| 6,213,398 B1 | 4/2001 | Southworth et al. | 235/254 |
| 6,274,980 B1 | 8/2001 | Burrows | 313/506 |
| 6,670,758 B1 * | 12/2003 | Beech et al. | 362/264 |
| 2002/0030194 A1 | 3/2002 | Cameras et al. | |
| 2002/0167485 A1 | 11/2002 | Hedrick | |
| 2003/0050534 A1 | 3/2003 | Kazakevich | |

* cited by examiner

Primary Examiner—Stephen F Husar
(74) Attorney, Agent, or Firm—McCracken & Frank LLP

(57) ABSTRACT

A light emitting device includes a hollow truncated spherical housing having an inner surface and an outer surface. The housing is substantially transparent. A light source, that generates a plurality of light rays, is positioned with respect to the housing to minimize an angle of incidence associated with each of the plurality of rays as they intersect the inner surface of the housing thereby minimizing the refractive effects of the housing as the rays of light generated by the light source pass through the housing.

51 Claims, 3 Drawing Sheets

PRECISION LIGHT EMITTING DEVICE

TECHNICAL FIELD

The present invention relates generally to a light emitting device and more particularly to a precision light emitting device that generates an intense light.

BACKGROUND OF THE INVENTION

The demand for increase in the precision of light emitting devices has increased as the applications for such devices have become increasingly sophisticated over time. Precision light emitting devices are often employed as point light sources in surgical environments to precisely locate the position of medical instruments in surgical navigation applications. Many manufacturing facilities also employ precision point light sources to derive position data with respect to the relative position of manufacturing tools. The military often use precision light emitting devices to update guidance and navigational data pertaining, for example, missile systems.

Camras et al., U.S. patent application No. 2002/0030194 A1 discloses a light emitting device including a transparent housing having a solid generally hemispherical shape. The light source is bonded to center point of the circle defined by the substantially flat surface of the transparent housing.

Hendrik, U.S. patent application No. 2002/0167485 discloses an image display generator for use in a heads-up display. An array of LEDs are formed on a semiconductor layer deposited on a surface, such as for example, glass. A sapphire sheet with a plurality of lens each having a solid hemispherical shape is disposed on the opposite surface of the glass. The sapphire sheet is aligned so that each LED is aligned with a corresponding sapphire lens.

Hsiong et al., U.S. Pat. No. 5,366,178 discloses the use of an transparent truncated solid hemispherical dome as a protective window for an infrared sensor.

SUMMARY OF THE INVENTION

According to one aspect of the present invention, a light emitting device includes a hollow truncated spherical housing. The housing is substantially transparent. A light source is positioned at a center point of a sphere defined by the spherical shape of the housing.

In accordance with a further aspect of the present invention, a light emitting device includes a hollow truncated spherical housing having an inner surface and an outer surface. The housing is substantially transparent. A light source, that generates a plurality of light rays, is positioned with respect to the housing to minimize an angle of incidence associated with each of the plurality of light rays as they intersect the inner surface of the housing.

Other aspects and advantages of the present invention will become apparent upon consideration of the following detailed description.

DESCRIPTION OF THE PREFERRED EMBODIMENTS

Figure 1:
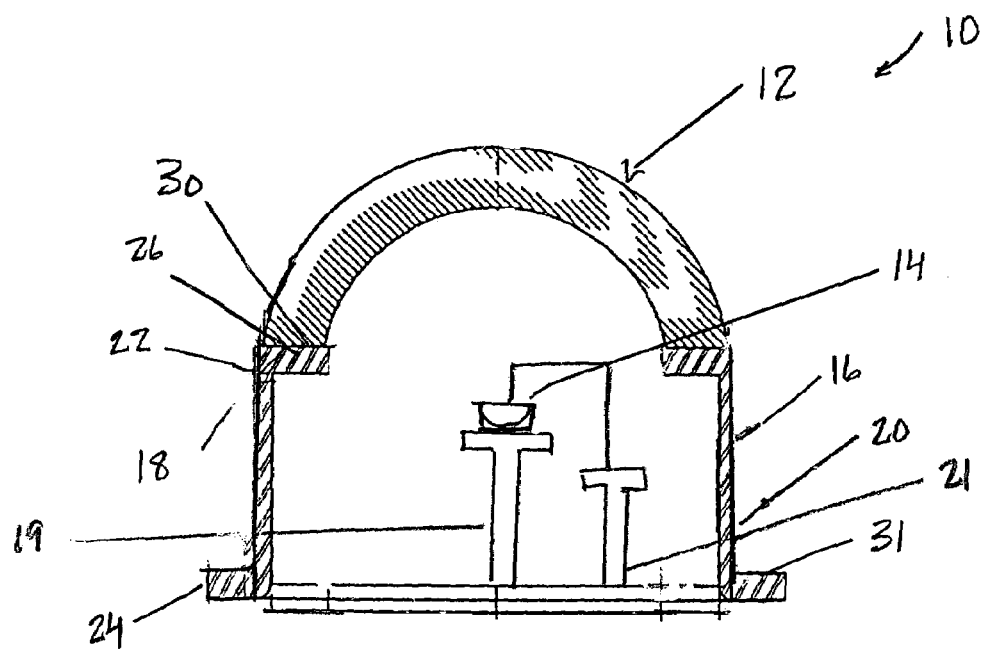
FIG. 1 is a cross-sectional side view of a precision light emitting device.
Figure 2:
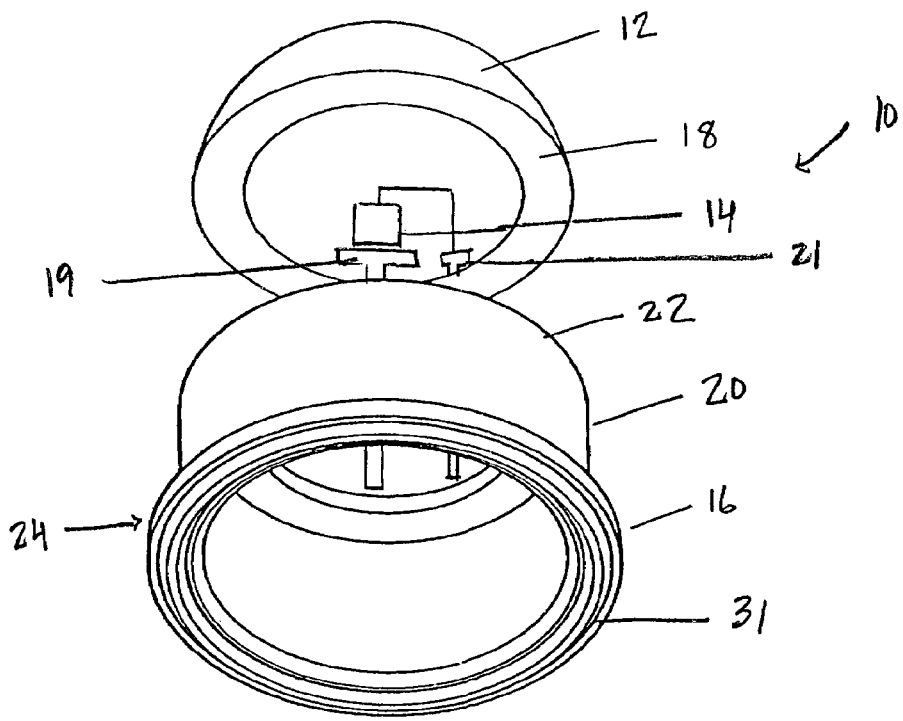
FIG. 2 is an exploded view of the precision light emitting device of FIG. 1.

Referring to FIGS. 1 and 2, a precision light emitting device 10, generally includes a substantially transparent housing 12, a light source 14 and a housing base 16. The transparent housing 12 is hollow and in the shape of a truncated sphere, preferably a truncated hemisphere, terminating in an annular surface 18.

The light source 14 preferably comprises an infrared light emitting diode (LED). The infrared LED used may include a Galium Arsenide LED. However, the use of other types of light sources, including but not limited to, other solid state or semiconductor light sources, incandescent light sources and laser light sources are also considered to be within the spirit of the invention. Also while an infrared light source is described, light sources adapted to generate alternative desired wavelengths are also considered to be within the scope of the invention.

The LED light source 14 is mounted on a mounting pin 19 using a conductive bonding agent, such as for example, epoxy. Bonding techniques using other conductive bonding agents, as are known to those having ordinary skills in the art, may be used to bond the LED light source 14 to the mounting pin 19. A second pin 21 is provided to electrically couple the LED light source 14 to a power source.

The housing base 16 consists of a hollow generally cylindrical body 20 having an upper end 22 and a lower end 24. The upper end 22 terminates in an inwardly extending flange 26. The transparent housing 12 sits on the inwardly extending flange 26. The lower end 24 of the housing base 16 terminates in an outwardly extending flange 31.

In another embodiment, an annular lip may extend upward from the outer boundary of the inwardly extending flange 26. The transparent housing 12 may sit within an annular recess defined by the annular lip and inwardly extending flange 26.

In another embodiment, an annular ring may extend outward from the outwardly extending flange 31.

It should be noted that while a preferred structure of the housing base 16 has been described, alternative housing base structures for supporting the transparent housing 12 are also considered to be within the scope of the invention.

Figure 3:
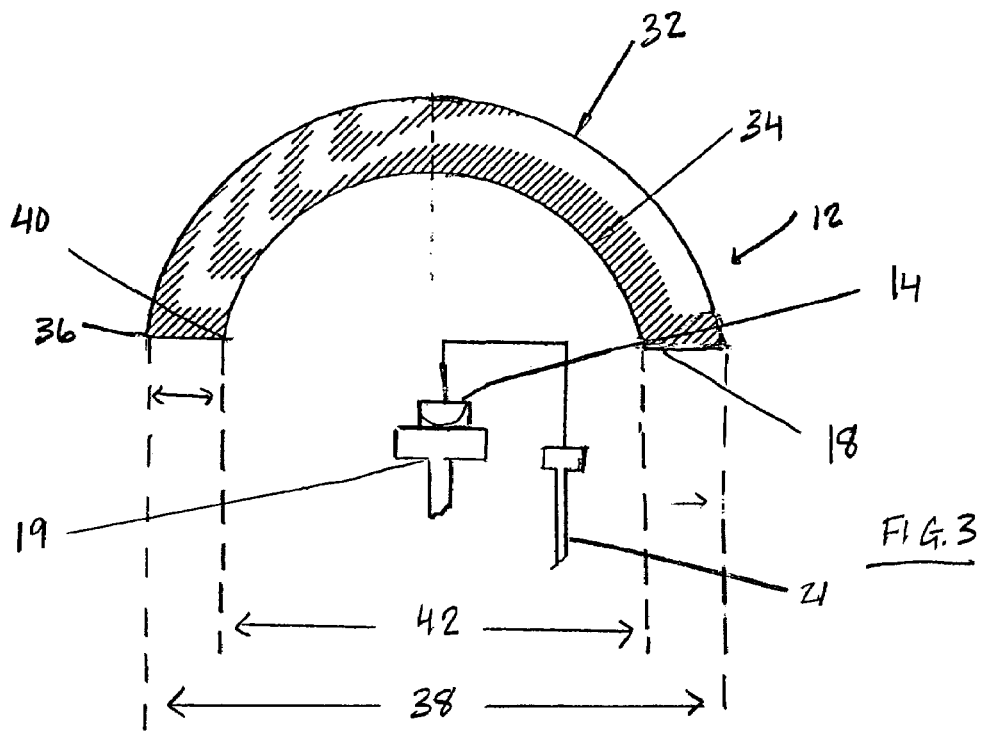
FIG. 3 is a cross-sectional side view of the transparent housing of FIG. 1.

Referring to FIG. 3, as mentioned previously, the transparent housing 12 is hollow and preferably in the shape of a truncated hemisphere terminating in an annular surface 18. The transparent housing 12 preferably comprises a crystalline substance that is able to withstand autoclave temperatures, such as for example, sapphire. In alternative embodiments, the transparent housing 12 may comprise one of several different materials including but not limited to glass, quartz, diamond, polymethylmethacrylate, silicone or Pyrex glass.

The transparent housing 12 preferably has a generally uniform thickness that is preferably about the same as the width of the inwardly extending flange 26. The transparent housing 12 is designed to minimize the loss of light emitted by the light source 14 as it passes through the transparent housing 12. While a preferred embodiment the transparent housing 12 has a generally uniform thickness of about 1.2 mm, the thickness of the transparent housing may range from about 1.2 mm to about 12.7 mm without departing from the spirit of the invention. The transparent housing 12 has a polished outer surface 32 and an inner surface 34. While the outer circle defined by the outer edge 36 of the annular surface 18 preferably has an outer diameter 38 of about 4.4 mm, the outer diameters 38 ranging from about 4.4 mm to about 25.4 mm are also considered to be within the scope of the invention. The inner circle defined by the inner edge 40 of the annular surface 18 preferably has an inner diameter 42 of about 3.2 mm but other diameters may be employed without departing from the spirit of the invention. It should be noted that while a preferred range of inner and outer diameters have been provided for a transparent sapphire housing, inner and/or outer diameters having lesser and/or greater values are also considered to be within the scope of the invention. Furthermore, transparent housings constructed from alternative materials may have inner and/or outer diameters having lesser and/or greater values.

Also while a preferred embodiment of the transparent housing 12 has a generally truncated hemispherical shape, alternative shapes of transparent housing, such as for example, variations of a hollow truncated sphere including a hollow hemisphere are also considered to be within the scope of the invention.

The light source 14 is positioned with respect to the transparent housing 12 to minimize the angle of incidence as the plurality of light rays generated by the light source 14 intersect the inner surface 34 of the transparent housing 12, thereby reducing the refractive effects of the transparent housing 12 on the light rays as they pass through the transparent housing 12. Minimizing the refractive effects of the transparent housing 12 on the light rays as they pass through the transparent housing 12 typically generates a more intense light source. More specifically, the light source 14 is positioned at a center-point, or a focal point, of a virtual sphere as defined by the spherical curvature of the transparent housing 12.

Figure 4:
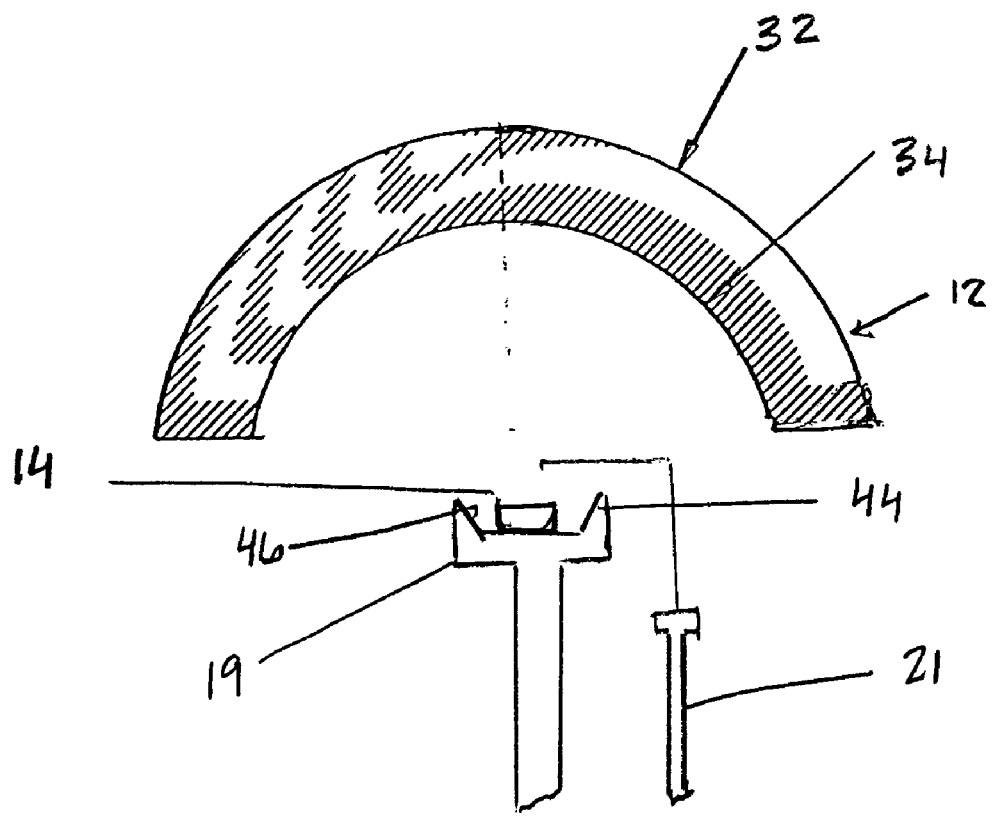
FIG. 4 is a cross-sectional side view of a light source positioned with respect to a truncated semi-elliptical shaped reflective surface.

Referring to FIG. 4, another embodiment of the precision light emitting device includes a reflector 44. The reflector 44 is generally bowl shaped having a generally flat bottom surface with an outwardly extending angled wall 46. The reflecting surfaces are preferably gold coated surfaces when using an infrared light source 14. However the use of alternative coating agents are also considered to be within the scope of the invention. The light source 14 is positioned between the reflective surface 46 and the transparent housing 12 such that a substantial amount of the light rays generated by the light source 14 in the direction of the reflective surface 46 are reflected back towards the transparent housing 12 thereby increasing the intensity of the light generated by the light emitting device 10. The light source 14 is preferably positioned such that its upper surface of the light source 14 is about flush with or below the upper edges of the reflector 44.

While one embodiment of a reflector 44 is shown, other forms of reflective surfaces, including but not limited to, the inner surface or a truncated semi-elliptical reflective surface 46, the inner surface of a hemispherical shaped reflective surface or a planar shaped reflective surface are also considered to be within the scope of the invention.

In operation, once the light source 14 is turned on, a plurality of the light rays generated by the light source 14 travel in a direction towards either the transparent housing 12 or the reflective surface 46. The positioning of the light source 14 at the focal point of a sphere defined by the curvature of the transparent housing 12 causes the plurality of light rays traveling in the direction of the transparent housing 12 to intersect the inner surface 34 of the transparent housing 12 at a reduced angle of incidence, preferably approaching a normal angle. This permits the plurality of light rays to pass through the transparent housing 12 at a substantially normal angle thereby reducing the refractive effects of the transparent housing 12 on the plurality of light rays and increasing the intensity of the light source 14. The plurality of light rays impacting the surface of the reflective surface 46 are reflected back towards the transparent housing 12 thereby further increasing the intensity of the light source 14.

Numerous modifications will be apparent to those skilled in the art in view of the foregoing description. Accordingly, this description is to be construed as illustrative only and is presented for the purpose of enabling those skilled in the art to make and use the invention and to teach the best mode of carrying out the same. The exclusive rights to all such modifications which come within the scope of the appended claims are reserved.

I claim:

1. A light emitting device, comprising:
    a hollow truncated spherical housing, the housing being substantially transparent and being formed from a crystalline substance;
    a light source positioned at a center point of a sphere defined by a spherical curvature of the housing; and
    a hollow cylindrical housing base having sidewalls of substantially uniform thickness, wherein the housing sits on the housing base.

2. The light emitting device of claim 1, wherein the hollow truncated spherical housing comprises a hollow hemispherical housing.

3. The light emitting device of claim 1, where the hollow truncated spherical housing comprises a hollow truncated hemispherical housing.

4. The light emitting device of claim 1, wherein the housing is of a substantially uniform thickness.

5. The light emitting device of claim 1, wherein the housing is of a substantially uniform thickness of about 1.2 mm.

6. The light emitting device of claim 1, wherein the housing is of a substantially uniform thickness and the thickness of the housing ranges from about 1.2 mm to about 12.7 mm.

7. The light emitting device of claim 1, wherein the housing terminates in a annular surface having an inner diameter of about 3.2 mm.

8. The light emitting device of claim 1, wherein the housing terminates in an annular surface having an outer diameter of about 4.4 mm.

9. The light emitting device of claim 1, wherein the housing terminates in an annular surface having an outer diameter ranging from about 4.4 mm to about 25.4 mm.

10. The light emitting device of claim 1, wherein the housing terminates in an annular surface wherein the width of the annular surface is about the same as the thickness of the housing.

11. The light emitting device of claim 1, wherein the crystalline substance is sapphire.

12. The light emitting device of claim 1, wherein the light source comprises a solid state light source.

13. The light emitting device of claim 1, wherein the light source comprises a Gallium Arsenide light emitting diode.

14. The light emitting device of claim 1, wherein the light source comprises a light emitting diode.

15. The light emitting device of claim 1, wherein the light source comprises an infrared light source.

16. The light emitting device of claim 1, wherein the light source comprise an incandescent light source.

17. The light emitting device of claim 1, wherein the light source comprises a laser light source.

18. The light emitting device of claim 1, further including a reflective surface, wherein the light source is disposed between the housing and the reflective surface.

19. The light emitting device of claim 18, wherein the reflective surface comprises a gold coated surface.

20. The light emitting device of claim 1, wherein the housing base has an upper end and a lower end, wherein the upper end terminates in an inwardly extending flange.

21. A light emitting device, comprising:
   a hollow truncated spherical housing having an inner surface and an outer surface, the housing being substantially transparent and being formed from a crystalline substance;
   a light source for generating a plurality of light rays, the light source being positioned with respect to the housing to minimize an angle of incidence associated with each of the plurality of light rays as they intersect the inner surface of the housing; and
   a hollow cylindrical housing base having sidewalls of substantially uniform thickness, wherein the housing sits on the housing base.

22. The light emitting device of claim 21, wherein the hollow truncated spherical housing comprises a hollow hemispherical housing.

23. The light emitting device of claim 21, wherein the hollow truncated spherical housing comprises a hollow truncated hemispherical housing.

24. The light emitting device of claim 21, wherein the housing is of a substantially uniform thickness.

25. The light emitting device of claim 21, wherein the housing is of a substantially uniform thickness of about 1.2 mm.

26. The light emitting device of claim 21, wherein the housing is of a substantially uniform thickness and the thickness of the housing ranges from about 1.2 mm to about 12.7 mm.

27. The light emitting device of claim 21, wherein the housing terminates in a annular surface having an inner diameter of about 3.2 mm.

28. The light emitting device of claim 21, wherein the housing terminates in an annular surface having an outer diameter of about 4.4 mm.

29. The light emitting device of claim 21, wherein the housing terminates in an annular surface having an outer diameter ranging from about 4.4 mm to about 25.4 mm.

30. The light emitting device of claim 21, wherein the housing terminates in an annular surface wherein the width of the annular surface is about the same as the thickness of the housing.

31. The light emitting device of claim 21, wherein the crystalline substance is sapphire.

32. The light emitting device of claim 21, wherein the light source comprises a solid state light source.

33. The light emitting device of claim 21, wherein the light source comprises a Gallium Arsenide light emitting diode.

34. The light emitting device of claim 21, wherein the light source comprises a light emitting diode.

35. The light emitting device of claim 21, wherein the light source comprises an infrared light source.

36. The light emitting device of claim 21, wherein the light source comprise an incandescent light source.

37. The light emitting device of claim 21, wherein the light source comprises a laser light source.

38. The light emitting device of claim 21, further including a reflective surface, wherein the Light source is disposed between the housing and the reflective surface.

39. The light emitting device of claim 38, wherein the reflective surface comprises a gold coated surface.

40. The light emitting device of claim 21, wherein the housing base has an upper end and a lower end, wherein the upper end terminates in an inwardly extending flange.

41. The light emitting device of claim 1, wherein the crystalline substance is diamond.

42. The light emitting device of claim 1, wherein the crystalline substance is quartz.

43. The light emitting device of claim 18, wherein the light source and the reflective surface are mounted on a conductive pin.

44. The light emitting device of claim 21, wherein the crystalline substance is diamond.

45. The light emitting device of claim 1, wherein the crystalline substance is quartz.

46. The light emitting device of claim 38, wherein the light source and the reflective surface are mounted on a conductive pin.

47. A light emitting device, comprising:
   a hollow truncated spherical housing, the housing being substantially transparent;
   a light source positioned at a center point of a sphere defined by a spherical curvature of the housing; and
   a hollow cylindrical housing base, wherein the housing sits on the housing base.

48. The light emitting device of claim 47, wherein the housing base has an upper end and a lower end, wherein the upper end terminates in an inwardly extending flange.

49. A light emitting device, comprising:
   a hollow truncated spherical housing having an inner surface and an outer surface, the housing being substantially transparent and being formed from a crystalline substance;
   a light emitting diode for generating a plurality of light rays, the light source being positioned with respect to the housing to minimize an angle of incidence associated with each of the plurality of light rays as they intersect the inner surface of the housing; and
   a hollow cylindrical housing base, wherein the housing sits on the housing base.

50. The light emitting device of claim 49, wherein the housing base has an upper end and a lower end, wherein the upper end terminates in an inwardly extending flange.

51. The light emitting device of claim 50, wherein the light emitting diode comprises an infrared light emitting diode.

* * * * *